US010918669B2

(12) United States Patent
Nobert

(10) Patent No.: US 10,918,669 B2
(45) Date of Patent: Feb. 16, 2021

(54) METHODS OF TREATING EXERCISE-INDUCED PULMONARY HEMORRHAGE

(71) Applicant: RECELLERATE, INC., Middleburg, VA (US)

(72) Inventor: Karl Nobert, Middleburg, VA (US)

(73) Assignee: RECELLERATE, INC., Middleburg, VA (US)

( * ) Notice: Subject to any disclaimer, the term of this patent is extended or adjusted under 35 U.S.C. 154(b) by 0 days.

(21) Appl. No.: 15/329,220

(22) PCT Filed: Jul. 24, 2015

(86) PCT No.: PCT/US2015/042105
§ 371 (c)(1),
(2) Date: Jan. 25, 2017

(87) PCT Pub. No.: WO2016/015007
PCT Pub. Date: Jan. 28, 2016

(65) Prior Publication Data

US 2017/0216361 A1 Aug. 3, 2017

Related U.S. Application Data

(60) Provisional application No. 62/029,310, filed on Jul. 25, 2014.

(51) Int. Cl.

| | |
|---|---|
| ***A61K 35/28*** | (2015.01) |
| ***A61K 9/00*** | (2006.01) |
| ***A61K 45/06*** | (2006.01) |
| ***A61K 31/138*** | (2006.01) |
| ***A61K 35/12*** | (2015.01) |
| ***A61K 31/519*** | (2006.01) |
| ***A61K 31/4704*** | (2006.01) |
| ***A61K 31/56*** | (2006.01) |
| ***A61K 31/439*** | (2006.01) |
| ***A61K 31/635*** | (2006.01) |
| ***A61K 31/198*** | (2006.01) |
| ***A61K 31/58*** | (2006.01) |
| ***A61K 31/137*** | (2006.01) |
| ***A61K 31/44*** | (2006.01) |
| ***A61K 31/573*** | (2006.01) |
| ***A61K 31/167*** | (2006.01) |

(52) U.S. Cl.
CPC ........... *A61K 35/28* (2013.01); *A61K 9/0078* (2013.01); *A61K 31/137* (2013.01); *A61K 31/138* (2013.01); *A61K 31/167* (2013.01); *A61K 31/198* (2013.01); *A61K 31/439* (2013.01); *A61K 31/44* (2013.01); *A61K 31/4704* (2013.01); *A61K 31/519* (2013.01); *A61K 31/56* (2013.01); *A61K 31/573* (2013.01); *A61K 31/58* (2013.01); *A61K 31/635* (2013.01); *A61K 35/12* (2013.01); *A61K 45/06* (2013.01)

(58) Field of Classification Search
None
See application file for complete search history.

(56) References Cited

U.S. PATENT DOCUMENTS

2011/0038903 A1 2/2011 Singh

FOREIGN PATENT DOCUMENTS

WO WO 2012/030968 A1 3/2012
WO WO 2012/125471 A1 9/2012

OTHER PUBLICATIONS

International Search Report and Written Opinion dated Oct. 29, 2015 for Application No. PCT/US2015/042105, 9 pages.

Kenneth W. Hinchcliff, "Exercise-Induced Pulmonary Hemorrhage", *Advances in Equine Nutrition*—vol. IV, *Kentucky Equine Research*, 2009, pp. 367-377.

*Primary Examiner* — David W Berke-Schlessel
(74) *Attorney, Agent, or Firm* — Seyfarth Shaw LLP

(57) ABSTRACT

Provided herein are methods of treating EIPH in a subject in need thereof. The methods comprise administering an effective amount of a pharmaceutical composition to the subject. In some embodiments, the pharmaceutical composition comprises a granuloma fluid, or a composition derived from a granuloma fluid. In some embodiments, the pharmaceutical composition comprises a cell. These pharmaceutical compositions may be administered by any suitable route of administration, and may be administered with one or more further therapeutic agents. Also provided are kits comprising pharmaceutical compositions for use with the methods provided herein.

16 Claims, No Drawings

METHODS OF TREATING EXERCISE-INDUCED PULMONARY HEMORRHAGE

CROSS REFERENCE

The present application is the U.S. national stage of International Application no. PCT/US2015/042105, filed Jul. 25, 2014, which claims the benefit of U.S. provisional application No. 62/029,310, filed Jul. 25, 2014, the content of each is hereby incorporated by reference in its entirety.

FIELD

Provided herein are methods for treating exercise-induced pulmonary hemorrhage in a subject. In some embodiments, the methods comprise the administration of a granuloma fluid to a subject in need thereof. In some embodiments, the methods comprise administration of a cell to a subject in need thereof.

BACKGROUND

Exercise-induced pulmonary hemorrhage (EIPH), also known as "bleeding" or a "bleeding attack," refers to the accumulation of blood in the airways of the lung in association with exercise. EIPH is common in horses undertaking intense exercise, but it has also been reported in human athletes, racing camels, and racing greyhounds. In thoroughbred racehorses, the estimated prevalence of EIPH is 43 to 75%. See Pascoe et al., *Amer. J. Vet. Res.*, 1981, 42:703-707, incorporated by reference in its entirety.

Animals with EIPH may be referred to as "bleeders" or as having "broken a blood vessels." In the majority of cases EIPH is not apparent unless an endoscopic examination of the airways is performed following exercise. However, some subjects may show bleeding at the nostrils after exercise, known as epistaxis.

A number of treatments have been used or suggested for EIPH, including resting, anti-inflammatories (e.g., corticosteroids), bronchodilators, anti-hypertensive agents (including nitric oxide donors and phosphodiesterase inhibitors), conjugated estrogens (e.g., Premarin®), antifibrinolytics (e.g., aminocaproic acid and tranexamic acid), snake venom, aspirin, vitamin K, bioflavinoids, diuretics (e.g., furosemide, known as Lasix® or Salix®), nasal strips, and omega-3 fatty acids.

Although furosemide is the most common treatment used in race horses, it is believed to be ineffective in a large number of subjects. Furosemide may also improve racing times in horses both with and without EIPH, possibly due to a lowering of body weight as a consequence of its potent diuretic action. The use of furosemide in competing horses is therefore prohibited in some countries, and it is regarded as a banned substance by the International Olympic Committee. Moreover, chronic usage of the drug can lead to hypokalemia and hypomagnesemia. Finally, the diuretic effects of furosemide can lead to dehydration, which can be detrimental to the health of subjects engaging in athletic activities.

There is therefore a need for new treatments for EIPH, with improved efficacy and fewer side-effects.

SUMMARY

Provided herein are methods of treating EIPH in a subject in need thereof.

In some embodiments, the method comprises administering an effective amount of a pharmaceutical composition comprising granuloma fluid, or a composition derived therefrom, to the subject. In some embodiments, the method comprises administering an effective amount of a pharmaceutical composition comprising a cell to the subject. In some embodiments, the cell is a stem cell. In some embodiments, the stem cell is a mesenchymal stem cell.

The pharmaceutical compositions can be administered systemically or locally. In some embodiments, the pharmaceutical composition is administered by a route of administration selected from the nasal, pulmonary, inhalation, intraarterial, intradermal, intramuscular, intraperitoneal, intravenous, parenteral, and subcutaneous routes. In some embodiments, the pharmaceutical compositions are administered by a route of administration selected from the nasal and pulmonary routes.

In some embodiments, the subject is selected from a horse, a dog, a camel, a monkey, a cat, a pig, a cow, a goat, a llama, a sheep, a mouse, a rat, a rabbit, and a human.

In some embodiments, the pharmaceutical composition is administered in combination with at least one further active agent.

Also provided are kits for carrying out the methods of treatment provided herein. In some embodiments, the kit comprises an effective amount of a pharmaceutical composition comprising granuloma fluid, or a composition derived therefrom. In some embodiments, the kit comprises an effective amount of a cell. In some embodiments, the cell is a stem cell. In some embodiments, the stem cell is a mesenchymal stem cell. In some embodiments, the kit comprises a nasal strip.

DESCRIPTION OF ILLUSTRATIVE EMBODIMENTS

Provided herein are methods of treating EIPH in a subject in need thereof. The methods comprise administering an effective amount of a pharmaceutical composition to the subject. In some embodiments, the pharmaceutical composition comprises a granuloma fluid, or a composition derived from a granuloma fluid. In some embodiments, the pharmaceutical composition comprises a cell. In some embodiments, the pharmaceutical composition comprises a granuloma fluid, or a composition derived from a granuloma fluid, and a cell. As described further elsewhere in this disclosure, these pharmaceutical compositions may be administered by any suitable route of administration, and may be administered with one or more further therapeutic agents. Also provided are kits comprising pharmaceutical compositions for use with the methods provided herein.

1. DEFINITIONS

As used herein, the term "about" refers to the stated value plus or minus 15%. For example, a value of "about 10" encompasses a range of 8.5 to 11.5.

As used herein, the term "granuloma fluid" refers to a fluid that is collected from the site of a granuloma. A granuloma forms when the immune system attempts to isolate a substance that it perceives as foreign but that it is unable to eliminate. A granuloma may be induced, for example, by implantation of a foreign body in a mammal. Fluid from the granuloma ("granuloma fluid") can be collected, for example, by utilizing a fluid collection device as the foreign body. The collection device can be introduced into any suitable tissue of an animal, such as an omentum or a subcutaneous tissue. The process of inducing granuloma formation and collecting fluid therefrom is described in more detail elsewhere in this disclosure and, for example, in U.S. Pat. Pub. No. 2011/0038903 A1, incorporated by reference in its entirety. The granuloma fluid resembles plasma, with respect to the major proteins (e.g., albumin and globulins), when analyzed by sodium dodecyl sulfate—polyacrylamide gel electrophoresis (SDS-PAGE).

As used herein, the term "composition derived from granuloma fluid" includes, for example, a powder produced from the granuloma fluid, a concentrated granuloma fluid, or a diluted granuloma fluid. A powder may be produced from granuloma fluid by, for example, drying (e.g., lyophilization), or by any other suitable method known in the art. A concentrated granuloma fluid may be produced by, for example, centrifugal filtration, or by any other suitable method known in the art. A diluted granuloma fluid may be produced by, for example, addition of a solvent to a granuloma fluid, or by any other suitable method known in the art.

As used herein, the term "granuloma powder" refers to a powder produced by drying the granuloma fluid. Generally, each milliliter of granuloma fluid yields about 5 to about 200 mg of granuloma powder. In some aspects, each milliliter of granuloma fluid yields about 10 to about 100 mg of granuloma powder. In some aspects, each milliliter of granuloma fluid yields about 25 to about 75 mg of granuloma powder. In some aspects, each milliliter of granuloma fluid yields about 75 to about 100 mg of granuloma powder. In some embodiments, each milliliter of granuloma fluid yields about 50 mg of granuloma powder. In some aspects, each milliliter of granuloma fluid yields about 75 mg of granuloma powder.

As used herein, the term "granuloma cells" refers to the cells that are present at the site of a granuloma. These cells include any cell type that is present at the site of the granuloma, including stem cells (e.g., omental stem cells, subcutaneous granulation tissue stem cells, bone marrow derived mesenchymal stem cells), progenitor cells, or any other cell found at the site of a granuloma.

As used herein, "treating" or "treatment" of a disease or disorder refers, in certain embodiments, to ameliorating a disease or disorder that exists in a subject. In some embodiments, "treating" or "treatment" includes ameliorating at least one physical parameter, which may be indiscernible by the subject. In some embodiments, "treating" or "treatment" includes modulating the disease or disorder, either physically (e.g., stabilization of a discernible symptom) or physiologically (e.g., stabilization of a physical parameter) or both. In some embodiments, "treating" or "treatment" includes delaying or preventing the onset of the disease or disorder. In some embodiments, "treating" or "treatment" includes mitigating the incidence of a disease or disorder, by periodic administration of a pharmaceutical composition.

As used herein, the term "therapeutically effective amount" or "effective amount" refers to an amount of a composition provided herein that is useful for treating or preventing EIPH, or a symptom thereof. In some embodiments, the symptom is selected from epistaxis, blood in the pulmonary system, pulmonary hypertension, decrease in athletic performance, abnormal breathing during exercise, repeated swallowing, lack of appetite and combinations thereof.

As used herein, the term "subject" means a mammalian subject. Exemplary subjects include, but are not limited to horses, monkeys, dogs, cats, mice, rats, rabbits, camels, cows, goats, llamas, sheep, and humans. In certain embodiments, the subject is a horse. In some embodiments, the subject is a human. In some embodiments, the subject has been diagnosed with EIPH. In some embodiments, the subject is suspected to have EIPH. In some embodiments, the subject is at risk for developing EIPH. In some embodiments, a subject with EIPH is identified by epistaxis. In some embodiments, the subject is identified by endoscopy, bronchoalveolar lavage, biopsy, radiograph, and/or pulmonary scintigraphy. In some embodiments, a subject at risk for developing EIPH is identified by a history of EIPH, or by an elevated pulmonary blood pressure.

2. METHODS OF TREATING EIPH

Provided herein are methods of treating EIPH in a subject in need thereof. The methods comprise administering an effective amount of a pharmaceutical composition to the subject. In some embodiments, the pharmaceutical composition comprises a granuloma fluid, or a composition derived from a granuloma fluid. In some embodiments, the pharmaceutical composition comprises a cell. In some embodiments, the cell is a stem cell. In some embodiments, the stem cell is a mesenchymal stem cell.

In some embodiments, the pharmaceutical composition comprises a granuloma fluid, or a composition derived from a granuloma fluid. Accordingly, in some embodiments, provided herein are methods of treating EIPH in a subject in need thereof by administering an effective amount of a pharmaceutical composition comprising a granuloma fluid, or a composition derived from a granuloma fluid, to the subject. The pharmaceutical composition comprising the granuloma fluid, or composition derived therefrom, can be administered in any suitable dose or by any suitable route of administration. It can also be administered with any suitable further agent. Suitable doses, routes of administration, and further agents are described elsewhere in this disclosure.

In some embodiments, the pharmaceutical composition comprises a cell. Accordingly, in some embodiments, provided herein are methods of treating EIPH in a subject in need thereof by administering an effective amount of a pharmaceutical composition comprising a cell to the subject. The pharmaceutical composition comprising the cell can be administered in any suitable dose or by any suitable route of administration. It can also be administered with any suitable further agent. Suitable doses, routes of administration, and further agents are described elsewhere in this disclosure.

In some embodiments, the pharmaceutical composition comprises a stem cell. Accordingly, in some embodiments, provided herein are methods of treating EIPH in a subject in need thereof by administering an effective amount of a pharmaceutical composition comprising a stem cell to the subject. The pharmaceutical composition comprising the stem cell can be administered in any suitable dose or by any suitable route of administration. It can also be administered with any suitable further agent. Suitable doses, routes of administration, and further agents are described elsewhere in this disclosure.

In some embodiments, the pharmaceutical composition comprises a mesenchymal stem cell. Accordingly, in some embodiments, provided herein are methods of treating EIPH in a subject in need thereof by administering an effective amount of a pharmaceutical composition comprising a mesenchymal stem cell to the subject. The pharmaceutical composition comprising the mesenchymal stem cell can be administered in any suitable dose or by any suitable route of administration. It can also be administered with any suitable further agent. Suitable doses, routes of administration, and further agents are described elsewhere in this disclosure.

In some embodiments, the pharmaceutical composition comprises a granuloma fluid, or a composition derived from a granuloma fluid and a cell. Accordingly, in some embodiments, provided herein are methods of treating EIPH in a subject in need thereof by administering an effective amount of a pharmaceutical composition comprising a granuloma fluid, or a composition derived from a granuloma fluid, and a cell to the subject. The pharmaceutical composition comprising the granuloma fluid, or composition derived from granuloma fluid, and cell can be administered in any suitable dose or by any suitable route of administration. It can also be administered with any suitable further agent. Suitable doses, routes of administration, and further agents are described elsewhere in this disclosure. In some embodiments, the cell is a stem cell. In some embodiments, the stem cell is a mesenchymal stem cell.

In some embodiments, provided are methods of treating EIPH by administering an amount of a pharmaceutical composition that is effective to reduce the severity of EIPH on a grading system. Any suitable grading system may be used to evaluate EIPH. In some embodiments, the grading system is an endoscopic grading system that ranges from 0 to 4, with the following characteristics: Grade 0: no blood detected; Grade 1: one or more flecks of blood or ≤2 short, narrow streams (<10% of tracheal surface); Grade 2: one long stream or >2 short streams occupying less than 33% of tracheal circumference; Grade 3: multiple distinct streams of blood, covering greater than 33% of tracheal circumference; and Grade 4: multiple, coalescing streams of blood, covering more than 90% of the tracheal surface with blood pooling at the thoracic inlet. See Pascoe et al., *Amer. J. Vet. Res.*, 1981, 42:703-707; Mason et al., "Exercise-induced pulmonary haemorrhage in horses," in D. H. Snow et al. (Eds.), *Equine Exercise Physiology*, pp. 57-63, Granata Editions, Cambridge; Pascoe et al., *Amer. J. Vet. Res.*, 1985, 46:2000-2003; and Lapointe et al., *Equine Vet. J.*, 1994, 26:482-485, each of which is incorporated by reference in its entirety.

In some aspects, the severity of EIPH is reduced from a 4 to a 0. In some aspects, the severity of EIPH is reduced from a 4 to a 1. In some aspects, the severity of EIPH is reduced from a 4 to a 2. In some aspects, the severity of EIPH is reduced from a 4 to a 3.

In some aspects, the severity of EIPH is reduced from a 3 to a 0. In some aspects, the severity of EIPH is reduced from a 3 to a 1. In some aspects, the severity of EIPH is reduced from a 3 to a 2.

In some aspects, the severity of EIPH is reduced from a 2 to a 0. In some aspects, the severity of EIPH is reduced from a 2 to a 1.

In some aspects, the severity of EIPH is reduced from a 1 to a 0.

3. DOSES, UNIT DOSAGE FORMS, AND DOSING SCHEDULES

The clinician (e.g., veterinarian or physician) will determine the dose, unit dosage form, and dosing schedule that is most appropriate for the subject based on, for example, whether the treatment is preventative or curative, and the age, weight, and disease state of the subject. Illustrative doses, unit dosage forms, and dosing schedules are provided below.

3.1. Doses of Granuloma Fluid and Compositions Derived Therefrom, and Unit Dosage Forms Comprising Granuloma Fluid and Compositions Derived Therefrom As discussed above, a particular volume of granuloma fluid generally yields a particular mass of granuloma powder when dried. The mass of granuloma powder remaining when the granuloma fluid is dried varies, but is generally in the range of about 5 mg to about 200 mg per milliliter of granuloma fluid, more particularly from about 25 mg to about 75 mg per milliliter of granuloma fluid. Accordingly, in some embodiments, the dose of granuloma fluid, or composition derived therefrom, can be calculated based on an equivalent dose of granuloma powder.

For example, if a pharmaceutical composition comprises granuloma fluid itself, then a 1 milliliter dose of granuloma fluid may comprise an equivalent does of granuloma powder that ranges from about 5 mg to about 200 mg, or more particularly from about 25 mg to about 75 mg. On the other hand, if the pharmaceutical composition comprises granuloma powder, then the dose can be determined based on the mass of the granuloma powder itself. The equivalent dose of granuloma powder for a granuloma fluid can be determined by drying the granuloma fluid and weighing the resulting powder.

In some embodiments, the pharmaceutical composition comprises granuloma fluid. In some embodiments, the pharmaceutical composition comprises granuloma powder. In some embodiments, the pharmaceutical composition comprises a concentrated granuloma fluid. In some embodiments, the pharmaceutical composition comprises a diluted granuloma fluid.

In some embodiments, the dose of granuloma fluid, or composition derived therefrom, administered to the subject is equivalent to about 1 mg to about 20 g of granuloma powder. In some aspects, the dose is equivalent to about 10 mg to about 20 g of granuloma powder. In some aspects, the dose is equivalent to about 100 mg to about 20 g of granuloma powder. In some aspects, the dose is equivalent to about 500 mg to about 20 g of granuloma powder. In some aspects, the dose is equivalent to about 1 g to about 20 g of granuloma powder. In some aspects, the dose is equivalent to about 5 g to about 20 g of granuloma powder. In some aspects, the dose is equivalent to about 10 g to about 20 g of granuloma powder. In some aspects, the dose is equivalent to about 1 mg to about 10 g of granuloma powder. In some aspects, the dose is equivalent to about 1 mg to about 5 g of granuloma powder. In some aspects, the dose is equivalent to about 1 mg to about 1 g of granuloma powder. In some aspects, the dose is equivalent to about 1 mg to about 500 mg of granuloma powder. In some aspects, the dose is equivalent to about 1 mg to about 100 mg of granuloma powder. In some aspects, the dose is equivalent to about 1 mg to about 10 mg of granuloma powder. In some aspects, the dose is equivalent to about 200 mg to about 5 g of granuloma powder. In some aspects, the dose is equivalent to about 200 mg to about 2.5 g of granuloma powder. In some aspects, the dose is equivalent to about 200 mg to about 1 g of granuloma powder.

In some embodiments, the dose of granuloma fluid, or composition derived therefrom, may vary depending on the body weight of the subject. In some embodiments, the dose is equivalent to about 0.01 mg/kg to about 1 g/kg of granuloma powder. In some aspects, the dose is equivalent to about 0.1 mg/kg to about 1 g/kg of granuloma powder. In some aspects, the dose is equivalent to about 1 mg/kg to about 1 g/kg of granuloma powder. In some aspects, the dose is equivalent to about 5 mg/kg to about 1 g/kg of granuloma powder. In some aspects, the dose is equivalent to about 10 mg/kg to about 1 g/kg of granuloma powder. In some aspects, the dose is equivalent to about 50 mg/kg to about 1 g/kg of granuloma powder. In some aspects, the dose is equivalent to about 100 mg/kg to about 1 g/kg of granuloma powder. In some aspects, the does is equivalent to about 250 mg/kg to about 1 g/kg of granuloma powder. In some aspects, the does is equivalent to about 500 mg/kg to about 1 g/kg of granuloma powder. In some aspects, the dose is equivalent to about 0.1 mg/kg to about 500 mg/kg of granuloma powder. In some aspects, the dose is equivalent to about 0.1 mg/kg to about 250 mg/kg of granuloma powder. In some aspects, the dose is equivalent to about 0.1 mg/kg to about 100 mg/kg of granuloma powder. In some aspects, the dose is equivalent to about 0.1 mg/kg to about 50 mg/kg of granuloma powder. In some aspects, the dose is equivalent to about 0.1 mg/kg to about 25 mg/kg of granuloma powder. In some aspects, the dose is equivalent to about 0.1 mg/kg to about 10 mg/kg of granuloma powder. In some aspects, the dose is equivalent to about 0.1 mg/kg to about 5 mg/kg of granuloma powder. In some aspects, the dose is equivalent to about 0.1 mg/kg to about 1 mg/kg of granuloma powder.

In some embodiments, the pharmaceutical composition is in the form of a unit dosage that comprises a particular dose of granuloma fluid, or composition derived therefrom. The amount of granuloma fluid, or composition derived therefrom, in the unit dosage form will vary depending on the route of administration and other factors recognized by one of skill in the art.

In some embodiments, the unit dosage form comprises a dose equivalent to about 10 mg to about 20 g of granuloma powder. In some aspects, the unit dosage form comprises a dose equivalent to about 50 mg to about 20 g of granuloma powder. In some aspects, the unit dosage form comprises a dose equivalent to about 100 mg to about 20 g of granuloma powder. In some aspects, the unit dosage form comprises a dose equivalent to about 250 mg to about 20 g of granuloma powder. In some aspects, the unit dosage form comprises a dose equivalent to about 500 mg to about 20 g of granuloma powder. In some aspects, the unit dosage form comprises a dose equivalent to about 1 g to about 20 g of granuloma powder. In some aspects, the unit dosage form comprises a dose equivalent to about 5 g to about 20 g of granuloma powder. In some aspects, the unit dosage form comprises a dose equivalent to about 10 g to about 20 g of granuloma powder. In some aspects, the unit dosage form comprises a dose equivalent to about 15 g to about 20 g of granuloma powder. In some aspects, the unit dosage form comprises a dose equivalent to about 50 mg to about 15 g of granuloma powder. In some aspects, the unit dosage form comprises a dose equivalent to about 50 mg to about 10 g of granuloma powder. In some aspects, the unit dosage form comprises a dose equivalent to about 50 mg to about 5 g of granuloma powder. In some aspects, the unit dosage form comprises a dose equivalent to about 50 mg to about 1 g of granuloma powder. In some aspects, the unit dosage form comprises a dose equivalent to about 50 mg to about 500 mg of granuloma powder. In some aspects, the unit dosage form comprises a dose equivalent to about 50 mg to about 250 mg of granuloma powder. In some aspects, the unit dosage form comprises a dose equivalent to about 50 mg to about 100 mg of granuloma powder. In some aspects, the unit dosage form comprises a dose equivalent to about 5 mg, 10 mg, 25 mg, 50 mg, 100 mg, 250 mg, 500 mg, 1 g, 5 g, 10 g, 15 g, or 20 g of granuloma powder.

3.2. Doses of Cells and Unit Dosage Forms Comprising Cells

In some embodiments, the pharmaceutical composition comprises cells. In some embodiments, the cells are stem cells. In some embodiments, the stem cells are mesenchymal stem cells.

In some embodiments, the dose of cells administered to the subject is about $5\times10^4$ to about $5\times10^{11}$ cells. In some aspects, the dose of cells administered to the subject is about $5\times10^4$ to about $5\times10^{10}$ cells. In some aspects, the dose of cells administered to the subject is about $5\times10^4$ to about $5\times10^9$ cells. In some aspects, the dose of cells administered to the subject is about $5\times10^4$ to about $5\times10^8$ cells. In some aspects, the dose of cells administered to the subject is about $5\times10^4$ to about $5\times10^7$ cells. In some aspects, the dose of cells administered to the subject is about $5\times10^4$ to about $5\times10^6$ cells. In some aspects, the dose of cells administered to the subject is about $5\times10^4$ to about $5\times10^5$ cells. In some aspects, the dose of cells administered to the subject is about $5\times10^5$ to about $5\times10^{11}$ cells. In some aspects, the dose of cells administered to the subject is about $5\times10^6$ to about $5\times10^{11}$ cells. In some aspects, the dose of cells administered to the subject is about $5\times10^7$ to about $5\times10^{11}$ cells. In some aspects, the dose of cells administered to the subject is about $5\times10^8$ to about $5\times10^{11}$ cells. In some aspects, the dose of cells administered to the subject is about $5\times10^9$ to about $5\times10^{11}$ cells. In some aspects, the dose of cells administered to the subject is about $5\times10^{10}$ to about $5\times10^{11}$ cells.

In some embodiments, the dose of cells may vary depending on the body weight of the subject. In some embodiments, the dose is equivalent to about $5\times10^4$ cells/kg to about $5\times10^{11}$ cells/kg. In some aspects, the dose is equivalent to about $5\times10^5$ cells/kg to about $5\times10^{11}$ cells/kg. In some aspects, the dose is equivalent to about $5\times10^6$ cells/kg to about $5\times10^{11}$ cells/kg. In some aspects, the dose is equivalent to about $5\times10^7$ cells/kg to about $5\times10^{11}$ cells/kg. In some aspects, the dose is equivalent to about $5\times10^8$ cells/kg to about $5\times10^{11}$ cells/kg. In some aspects, the dose is equivalent to about $5\times10^9$ cells/kg to about $5\times10^{11}$ cells/kg. In some aspects, the dose is equivalent to about $5\times10^{10}$ cells/kg to about $5\times10^{11}$ cells/kg. In some aspects, the dose is equivalent to about $5\times10^4$ cells/kg to about $5\times10^{10}$ cells/kg. In some aspects, the dose is equivalent to about $5\times10^4$ cells/kg to about $5\times10^9$ cells/kg. In some aspects, the dose is equivalent to about $5\times10^4$ cells/kg to about $5\times10^8$ cells/kg. In some aspects, the dose is equivalent to about $5\times10^4$ cells/kg to about $5\times10^7$ cells/kg. In some aspects, the dose is equivalent to about $5\times10^4$ cells/kg to about $5\times10^6$ cells/kg. In some aspects, the dose is equivalent to about $5\times10^4$ cells/kg to about $5\times10^5$ cells/kg.

In some embodiments, the pharmaceutical composition is in the form of a unit dosage that comprises a particular dose of cells. The number of cells in the unit dosage form will vary depending on the route of administration and other factors recognized by one of skill in the art.

In some embodiments, the unit dosage form comprises about $5\times10^4$ to about $5\times10^{11}$ cells. In some aspects, the unit dosage form comprises about $5\times10^5$ to about $5\times10^{11}$ cells. In some aspects, the unit dosage form comprises about $5\times10^6$ to about $5\times10^{11}$ cells. In some aspects, the unit dosage form comprises about $5\times10^7$ to about $5\times10^{11}$ cells. In some aspects, the unit dosage form comprises about $5\times10^8$ to about $5\times10^{11}$ cells. In some aspects, the unit dosage form comprises about $5\times10^9$ to about $5\times10^{11}$ cells. In some aspects, the unit dosage form comprises about $5\times10^{16}$ to about $5\times10^{11}$ cells. In some aspects, the unit dosage form comprises about $5\times10^4$ to about $5\times10^{16}$ cells. In some aspects, the unit dosage form comprises about $5\times10^4$ to about $5\times10^9$ cells. In some aspects, the unit dosage form comprises about $5\times10^4$ to about $5\times10^8$ cells. In some aspects, the unit dosage form comprises about $5\times10^4$ to about $5\times10^7$ cells. In some aspects, the unit dosage form comprises about $5\times10^4$ to about $5\times10^6$ cells. In some aspects, the unit dosage form comprises about $5\times10^4$ to about $5\times10^5$ cells.

3.3. Dosing Schedules

The pharmaceutical composition may be administered to a subject according to any suitable dosing schedule. In some embodiments, the pharmaceutical composition is administered once. In some embodiments, the pharmaceutical composition is administered more than once.

In some embodiments, the pharmaceutical composition is administered according to a particular frequency. In some embodiments, the frequency is daily, every 2 days, every 3 days, every 4 days, every 5 days, every 6 days, every 7 days, every 8 days, every 9 days, every 10 days, every 11 days, every 12 days, every 13 days, or every 14 days. In some embodiments, the frequency is every 3 weeks, every 4 weeks, every 5 weeks, every 6 weeks, every 7 weeks, every 8 weeks, every 9 weeks, every 10 weeks, every 11 weeks, or every 12 weeks. In some embodiments, the frequency is every 1 month, every 2 months, every 3 months, every 4 months, every 5 months, every 6 months, every 7 months, every 8 months, every 9 months, every 10 months, every 11 months, every 12 months, every 13 months, every 14 months, every 15 months, every 16 months, every 17 months, or every 18 months. In some embodiments, the frequency is every 2 years, every 3 years, every 4 years, or every 5 years.

In some embodiments, the subject is treated over a particular duration of time. In some embodiments, the duration of treatment is from about 1 week to about 10 years. In some aspects, the duration of treatment is from about 1 week to about 5 years. In some aspects, the duration of treatment is from about 1 week to about 1 year. In some aspects, the duration of treatment is from about 1 week to about 6 months. In some aspects, the duration of treatment is from about 1 week to about 3 months. In some aspects, the duration of treatment is from about 1 week to about 1 month. In some aspects, the duration of treatment is from about 3 months to about 5 years. In some aspects, the duration of treatment is from about 6 months to about 5 years. In some aspects, the duration of treatment is from about 1 year to about 5 years.

Each dose may be administered over any suitable period of time. In some embodiments, the dose is administered as a bolus dose. In some embodiments, the dose is administered over a period of about 1 minute to about 4 hours. In some aspects, the dose is administered over a period of about 1 minute to about 2 hours. In some aspects, the dose is administered over a period of about 1 minute to about 1 hour. In some aspects, the dose is administered over a period of about 1 minute to about 30 minutes. In some aspects, the dose is administered over a period of about 1 minute to about 15 minutes.

In some embodiments, a dose is administered to a horse after a race. In some embodiments, a dose is administered to a horse periodically between races.

4. ROUTES OF ADMINISTRATION

The methods provided herein may be carried out by administering the pharmaceutical compositions by any suitable routes of administration. The route of administration can be local or systemic. Illustrative routes of administration include, for example, the nasal, pulmonary, inhalation, intraarterial, intradermal, intralesional, intramuscular, intraperitoneal, intravenous, intrathecal, intravesical, parenteral, rectal, subcutaneous, topical, transdermal, transmucosal, and vaginal routes.

In some embodiments, the pharmaceutical composition comprising a granuloma fluid, or a composition derived therefrom, is administered locally. In some embodiments, the pharmaceutical composition comprising a granuloma fluid, or a composition derived therefrom, is administered systemically.

In some embodiments, the pharmaceutical composition comprising a granuloma fluid, or a composition derived therefrom, is administered by a route of administration selected from the nasal, pulmonary, inhalation, intraarterial, intradermal, intralesional, intramuscular, intraperitoneal, intravenous, intrathecal, intravesical, parenteral, rectal, subcutaneous, topical, transdermal, transmucosal, and vaginal routes.

In some embodiments, the pharmaceutical composition comprising a granuloma fluid, or a composition derived therefrom, is administered by a route of administration selected from the nasal, pulmonary, inhalation, intraarterial, intradermal, intramuscular, intraperitoneal, intravenous, parenteral, and subcutaneous routes.

In some embodiments, the pharmaceutical composition comprising a granuloma fluid, or a composition derived therefrom, is administered by a route of administration selected from the nasal and pulmonary routes.

In some embodiments, the pharmaceutical composition comprising a cell is administered locally. In some embodiments, the pharmaceutical composition comprising a cell is administered systemically.

In some embodiments, the pharmaceutical composition comprising a cell is administered by a route of administration selected from the nasal, pulmonary, inhalation, intraarterial, intradermal, intralesional, intramuscular, intraperitoneal, intravenous, intrathecal, intravesical, parenteral, rectal, subcutaneous, topical, transdermal, transmucosal, and vaginal routes.

In some embodiments, the pharmaceutical composition comprising a cell is administered by a route of administration selected from the nasal, pulmonary, inhalation, intraarterial, intradermal, intramuscular, intraperitoneal, intravenous, parenteral, and subcutaneous routes.

In some embodiments, the pharmaceutical composition comprising a cell is administered by a route of administration selected from the nasal, pulmonary, inhalation, intraarterial, intradermal, intramuscular, intraperitoneal, and subcutaneous routes.

In some embodiments, the pharmaceutical composition comprising a cell is administered by a route of administration selected from the nasal and pulmonary routes.

In some embodiments, the pharmaceutical composition comprising a cell is not administered intravenously.

5. FURTHER THERAPEUTIC AGENTS

In some embodiments, the pharmaceutical composition comprises one or more further therapeutic agents. A further therapeutic agent may be, for example, a second therapeutic agent, a third therapeutic agent, a fourth therapeutic agent, a fifth therapeutic agent, or an additional therapeutic agent beyond a fifth therapeutic agent.

Any suitable further therapeutic agent may be used, and the selection of the further therapeutic agent is within the skill of the ordinary artisan. In some embodiments, the further therapeutic agent is selected from furosemide, aclidinium, albuterol, arformoterol, beclomethasone, budesonide, ciclesonide, clenbuterol, corticosteroids, dexamethasone, fluticasone, formoterol, indacaterol, ipratropium bromide, levalbuterol, L-arginine, metaproterenol, mometasone, pirbuterol, salmeterol, sildenafil, tiotropium, and vilanterol.

In some embodiments, the further therapeutic agent is serum or plasma. In some embodiments, the further therapeutic agent is platelet-rich plasma.

In some embodiments, the further therapeutic agent is a supernatant from a cultured cell, also known as a conditioned medium.

In some embodiments, the further therapeutic agent is a growth factor or cytokine. In some aspects the growth factor or cytokine is selected from VEGF, adrenomedullin, angiopoietin, autocrine motility factor, bone morphogenetic protein (BMP), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), healing factor, hepatocyte growth factor (HGF), hepatoma-derived growth factor (HDGF), insulin-like growth factor (IGF), interleukin-1 (IL-1), interleukin-6 (IL-6), keratinocyte growth factor (KGF), migration-stimulating factor, myostatin (GDF-8), nerve growth factor (NGF), neurotrophins, platelet-derived growth factor (PDGF), thrombopoietin (TPO), transforming growth factor alpha (TGF-$\alpha$), transforming growth factor beta (TGF-$\beta$), tumor necrosis factor-alpha (TNF-$\alpha$), and placental growth factor (PGF).

If further therapeutic agents are used, the doses of such agents can be obtained from the knowledge of those of skill in the art. For those further therapeutic agents that are approved for clinical use, recommended dosages are described in, for example, *Goodman & Gillman's The Pharmacological Basis of Therapeutics*, Brunton (Ed.) 12th Ed. (2010), McGraw-Hill New York; and *Physician's Desk Reference,* 67th Ed. (2013), PDR Network, each of which is incorporated by reference in its entirety.

In some embodiments, a pharmaceutical composition comprising granuloma fluid, or compositions derived therefrom, is administered at the same time as the further therapeutic agent. In some embodiments, a pharmaceutical composition comprising cells is administered at the same time as the further therapeutic agent. When the further therapeutic agent is administered at the same time as these pharmaceutical compositions, it can be included in the pharmaceutical composition, or administered in a separate pharmaceutical composition.

In some embodiments, a pharmaceutical composition comprising granuloma fluid, or compositions derived therefrom, is administered at a different time from the further therapeutic agent. In some embodiments, a pharmaceutical composition comprising cells is administered at a different time from the further therapeutic agent.

When the further therapeutic agent is administered at a different time than the pharmaceutical composition, the further therapeutic agent can be administered at any suitable time. In some embodiments, the further therapeutic agent and the pharmaceutical composition are administered less than 30 days apart, less than 15 days apart, less than 10 days apart, less than 5 days apart, less than 1 day apart, less than 12 hours apart, less than 6 hours apart, less than 3 hours apart, less than 1 hour apart, less than 30 minutes apart, or less than 15 minutes apart.

In some embodiments, the further therapeutic agent and the pharmaceutical composition are administered at least 15 minutes apart, at least 30 minutes apart, at least 1 hour apart, at least 3 hours apart, at least 6 hours apart, at least 12 hours apart, at least 1 day apart, at least 5 days apart, at least 10 days apart, at least 15 days apart, or at least 30 days apart.

In some embodiments, the pharmaceutical composition and the further therapeutic agent are administered within a time interval that allows them to have a synergistic therapeutic effect. This can be useful, for example, where the pharmaceutical composition or the further therapeutic agent has an undesirable side effect, because the synergy may allow a reduction in the dose of either or both.

In some embodiments, pharmaceutical composition is administered to a subject that is also treated with a nasal strip, a mechanical ventilation method, or a hyperbaric oxygen treatment (e.g., in a hyperbaric oxygen chamber).

6. PHARMACEUTICAL EXCIPIENTS

The pharmaceutical compositions used with the methods provided herein comprise granuloma fluid, compositions derived from granuloma fluid, or cells. In addition, the pharmaceutical compositions may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), The Pharmaceutical Press; and *Controlled Pulmonary Drug Delivery*, Smyth and Hickey (Eds.) (2011), Controlled Release Society, each of which is incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

In some embodiments, the pharmaceutical composition comprises a propellant. Illustrative examples of propellants include carbon dioxide, chlorodifluoromethane, chlorofluorocarbons, difluoroethane, dimethyl ether, heptafluoropropane, hydrocarbons (e.g., butane, isobutene, propane), nitrogen, nitrous oxide, and tetrafluoroethane.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press; and *Controlled Pulmonary Drug Delivery*, Smyth and Hickey (Eds.) (2011), Controlled Release Society, each of which is incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical composition comprises a macromolecule such as alginic acid, carboxymethylcellulose, carrageenan, chitosan, chondroitin sulfate, collagen, elastin, fibrin, fibronectin, gelatin, heparin sulfate, hyaluronic acid, keratin sulfate, laminin, Matrigel™, methylcellulose, poly(ethylene glycol), poly(lactic acid), poly(lactic-co-glycolic acid), and silk.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

7. KITS

Also provided are kits for use in the methods of treating EIPH provided herein.

In some embodiments, the kit comprises a pharmaceutical composition comprising granuloma fluid, or a composition derived from granuloma fluid. In some embodiments, the composition is a granuloma powder. In some embodiments, the powder is lyophilized powder. In some embodiments, the kit further comprises a pharmaceutically acceptable solution for reconstitution of the powder. In some embodiments, the solution is normal saline. In some embodiments, the kit further comprises instructions for the administration of the granuloma fluid or composition derived therefrom. In some embodiments, the kit further comprises a nasal strip.

In some embodiments, the kit further comprises a device for the administration of the granuloma fluid or composition derived therefrom. In some embodiments, the device is selected from a nebulizer, a nasal sprayer, a metered dose inhaler, a dry powder inhaler, a cannula, a tracheal tube, an endotracheal tube, a tracheostomy tube, an intranasal tube, and a needle. In some embodiments, the device comprises a needle for injecting the pharmaceutical composition. In some embodiments, the device is a device that generates an aerosol using a single-pass, low shear method. Such low shear methods may be useful for the delivery of labile molecules. Examples of single-pass, low shear aerosolization methods include the SUPRAER™ technology, by KAER Biotherapeutics. Such methods are more fully described, for example, in U.S. Pat. Nos. 7,802,569; 8,375,987; 8,596,268; 8,616,532; U.S. Pat. Pub. Nos. 2007/0144514; 2011/0006129; 2011/0011398; 2011/0011899; 2012/0017899; and 2013/0248615; and Yeates, "SUPRAER™: A New Class of Aerosol Delivery System for Biotherapeutics," *On Drug Delivery,* 2011, 12-14, each of which is incorporated by reference in its entirety.

In some embodiments, the kit comprises a pharmaceutical composition comprising cells. In some embodiments, the cells are stem cells. In some embodiments, the stem cells are mesenchymal stem cells. In some embodiments, the kit further comprises a pharmaceutically acceptable solution for addition to the cells prior to administration. In some embodiments, the solution is normal saline. In some embodiments, the kit further comprises instructions for the administration of the cells.

In some embodiments, the kit further comprises a device for the administration of the cells. In some embodiments, the device is selected from a nebulizer, a nasal sprayer, a metered dose inhaler, a dry powder inhaler, a cannula, a tracheal tube, an endotracheal tube, a tracheostomy tube, an intranasal tube, and a needle. In some embodiments, the device comprises a needle for injecting the pharmaceutical composition. In some embodiments, the device is a device adapted to deliver cells by pulmonary or nasal administration. Suitable devices for delivering cells by pulmonary or nasal administration include nasal sprays (see Shure, *Scientific American,* 2013, 24:14-15), endoscopes (see Ingenito et al., *Cell Transplantation,* 2012, 21:175-189), intratracheal instillation devices (see Gupta et al., *J. Immunol.,* 2007, 179:1855-1863; and Chang et al., *J. Korean Med. Sci.,* 2014, 29:438-440), transcutaneous transthoracic injection devices (see Lacis et al., *J. Sci. Res. Reports,* 2014, 3:1780-1792), or aerosolization devices (see Roberts, "Aerosol Delivery of Mammalian Cells for Tissue Engineering," Worcester Polytechnic Institute, Master of Science in Chemical Engineering Thesis, April, 2003; and Kardia et al., *J. Aerosol Med. & Pulmonary Drug Deliv.,* 2013, 26:1-5). Each of the references cited in this paragraph is incorporated by reference in its entirety.

8. GRANULOMA FLUID

In some embodiments, the pharmaceutical compositions used in the methods of treatment provided herein comprise granuloma fluid or a composition derived from granuloma fluid.

8.1. Collection of Granuloma Fluid

The granuloma fluid can be collected by using a hollow device, such as a tube, to induce the foreign body reaction, as described in U.S. Pat. Pub. No. 2011/0038903, incorporated by reference in its entirety. The device may have walls that are permeable to the granuloma fluid, thereby allowing the fluid to accumulate inside the hollow space of the device. The granuloma fluid may be harvested by removing the device from the animal, or by withdrawing fluid from the device while it remains inside the animal. The device can be implanted at any suitable site within the animal, including the omentum and subcutaneous tissue.

The device may be formed from any suitable material, including a flexible plastic, a hard plastic, or a metal. In some embodiments, the device is formed from a polyethylene or polyvinyl. The ends of the device may be sealed, to allow accumulation of fluid inside the device. The walls of the device may have holes, to allow the transport of fluid from the cells to the inside of the device.

The size of the device will vary according to the mammal in which it is to be implanted. A person of ordinary skill in the art can readily select a device of an appropriate size without undue experimentation, for example, depending on the size of the animal and the amount of fluid desired. For example, a device for implantation in a rat may have a length of about 10 to about 30 mm, a diameter of about 3.5 to 10.5 mm, and four to twelve holes of about 0.25 to about 0.75 mm. These dimensions may be scaled by any appropriate factor to estimate device sizes for other species. In some embodiments, the scaling may be according to the mass or volume of the animal relative to the mass or volume of another animal. In some embodiments, the scaling may be according to the volume of the implantation site relative to the volume of the corresponding implantation site in another animal.

Granuloma fluid may also be collected by injecting a slurry of particles. See U.S. Pat. Pub. No. 2011/0038903, incorporated by reference in its entirety. In some embodiments, the particles are polydextran particles. In some embodiments, the particles are injected subcutaneously. The subcutaneous injection of particles can create a "bladder-like" granulation tissue that can be pierced to withdraw granuloma fluid.

Granuloma fluid may also be collected by implanting a foam. In some embodiments, the foam is implanted subcutaneously or in the peritoneal cavity. The foam serves as a site for the formation of a granuloma. The granuloma fluid secreted by the cells is absorbed by the foam and can be retrieved from the foam by further processing, such as by squeezing the foam.

After collection, granuloma fluid may be processed by any suitable method, including centrifugation. In some aspects the granuloma fluid is separated from cells by centrifugation at 2000 g for 15 minutes, as described in U.S. Pat. Pub. No. 2011/0038903, incorporated by reference in its entirety.

8.2. Characteristics of Granuloma Fluid

The granuloma fluid resembles plasma when analyzed by SDS-PAGE. See U.S. Pat. Pub. No. 2011/0038903, incorporated by reference in its entirety. However, it also contains a variety of potent growth factors that are present at low concentrations (relative to albumin and globulins), and therefore are generally not detectable by SDS-PAGE.

In some embodiments, the granuloma fluid comprises vascular endothelial growth factor (VEGF) at a concentration of about 1 ng/mL to about 50 ng/mL. In some aspects, the granuloma fluid comprises VEGF at a concentration of about 2 ng/mL to about 25 ng/mL. In some aspects, the granuloma fluid comprises VEGF at a concentration of about 2 ng/mL to about 15 ng/mL. In some aspects, the granuloma fluid comprises VEGF at a concentration of about 2 ng/mL to about 7 ng/mL. In some aspects, the granuloma fluid comprises VEGF at a concentration of about 5 ng/mL to about 10 ng/mL. In some aspects, the granuloma fluid comprises VEGF at a concentration of about 5 ng/mL. In some aspects, the granuloma fluid comprises VEGF at a concentration of about 6 ng/mL. In some aspects, the granuloma fluid comprises VEGF at a concentration of about 7 ng/mL. In some aspects, the granuloma fluid comprises VEGF at a concentration of about 8 ng/mL. In some aspects, the granuloma fluid comprises VEGF at a concentration of about 9 ng/mL. In some aspects, the granuloma fluid comprises VEGF at a concentration of about 10 ng/mL. In some aspects, the granuloma fluid comprises VEGF at a concentration of about 11 ng/mL. In some aspects, the granuloma fluid comprises VEGF at a concentration of about 12 ng/mL.

In some embodiments, the granuloma fluid comprises VEGF at a concentration of about 5- to about 100-fold higher than the concentration of VEGF in the serum or plasma of the animal from which the granuloma fluid is derived. In some embodiments, the granuloma fluid comprises VEGF at a concentration of about 10- to about 80-fold higher than the concentration of VEGF in the serum or plasma of the animal from which the granuloma fluid is derived. In some embodiments, the granuloma fluid comprises VEGF at a concentration of about 20- to about 60-fold higher than the concentration of VEGF in the serum or plasma of the animal from which the granuloma fluid is derived. In some embodiments, the granuloma fluid comprises VEGF at a concentration of about 25- to about 50-fold higher than the concentration of VEGF in the serum or plasma of the animal from which the granuloma fluid is derived.

In some embodiments, the granuloma fluid comprises albumin at a concentration of about 1 g/L to about 100 g/L. In some embodiments, the granuloma fluid comprises albumin at a concentration of about 10 g/L to about 90 g/L. In some embodiments, the granuloma fluid comprises albumin at a concentration of about 20 g/L to about 80 g/L. In some embodiments, the granuloma fluid comprises albumin at a concentration of about 30 g/L to about 70 g/L. In some embodiments, the granuloma fluid comprises albumin at a concentration of about 35 g/L to about 50 g/L.

In some embodiments, the granuloma fluid comprises globulins at a concentration of about 1 g/L to about 100 g/L. In some embodiments, the granuloma fluid comprises globulins at a concentration of about 10 g/L to about 90 g/L. In some embodiments, the granuloma fluid comprises globulins at a concentration of about 20 g/L to about 80 g/L. In some embodiments, the granuloma fluid comprises globulins at a concentration of about 30 g/L to about 70 g/L. In some embodiments, the granuloma fluid comprises globulins at a concentration of about 26 g/L to about 46 g/L.

In some embodiments, the granuloma fluid comprises total protein at a concentration of about 1 g/L to about 100 g/L. In some embodiments, the granuloma fluid comprises total protein at a concentration of about 10 g/L to about 90 g/L. In some embodiments, the granuloma fluid comprises total protein at a concentration of about 20 g/L to about 80 g/L. In some embodiments, the granuloma fluid comprises total protein at a concentration of about 40 g/L to about 80 g/L. In some embodiments, the granuloma fluid comprises total protein at a concentration of about 60 g/L to about 80 g/L.

In some embodiments, the granuloma fluid is processed by a method that alters the amount of one or more of its components. Any suitable processing method may be used. Illustrative processing methods include dialysis, size filtration (such as centrifugal filtration), chromatography (such as size exclusion chromatography), and electrophoresis.

In some embodiments, the granuloma fluid is processed to alter the amount of albumin. The molecular weight of albumin varies by species, but generally ranges from about 55 kDa to about 80 kDa, or about 65 kDa to about 70 kDa. Accordingly, the amount of albumin in the granuloma fluid can be reduced by performing one or more fractionation steps that remove proteins in the molecular weight range appropriate for the species from which the granuloma fluid is collected. In some aspects, the amount of albumin in the processed granuloma fluid is reduced by at least about 10%, at least about 20%, at least about 30%, at least about 40%, at least about 50%, at least about 60%, at least about 70%, at least about 80%, at least about 90%, or at least about 95% in comparison to the granuloma fluid as harvested from the animal.

In some embodiments, the granuloma fluid is processed to alter the amount of VEGF. The amount of VEGF in the granuloma fluid can be reduced by, for example, molecular weight fractionation or by affinity-based methods using reagents that are specific for VEGF. In some aspects, the amount of VEGF in the processed granuloma fluid is reduced by at least about 10%, at least about 20%, at least about 30%, at least about 40%, at least about 50%, at least about 60%, at least about 70%, at least about 80%, at least about 90%, or at least about 95% in comparison to the granuloma fluid as harvested from the animal.

Reducing the amount(s) of albumin in the granuloma fluid will also reduce the amount of total protein in the fluid. Reduction of the amount of total protein may be useful, for example, to reduce the amount of anti-foaming agent that is used in certain formulations.

Cells for the production of granuloma fluid can be obtained from any suitable mammal. Suitable mammals include, for example, horses, dogs, cats, camels, pigs, cows, goats, llamas, sheep, mice, rats, rabbits, and humans. In some aspects, the mammal is a horse. In some aspects the mammal is a human.

9. CELLS

In some embodiments, the pharmaceutical compositions used in the methods of treatment provided herein comprise cells. In some embodiments, the cells are stem cells. In some embodiments the stem cells are embryonic stem cells. In some embodiments the stem cells are adult stem cells. In some embodiments, the stem cells are mesenchymal stem cells.

In some embodiments, the cell is selected from a macrophage, a lymphocyte, a neutrophil, an eosinophil, a multinucleated giant cell, and a fibroblast, and combinations thereof.

In some embodiments, the cells are cells collected with the granuloma fluid. Any cell proximal to the site of the granuloma may be useful with the methods of treatment provided herein.

In some embodiments, the foreign body used to collect the granuloma fluid may also be used to collect cells. The cells may be isolated from the proximity of the foreign body, or from the portion of the foreign body used to collect the granuloma fluid (e.g., the cavity of a tube). Collection of cells from a granuloma is discussed, for example, in U.S. Pat. Pub. No. 2011/0038903, incorporated by reference in its entirety.

Mesenchymal stem cells can be identified by the presence of a variety of markers, and by canonical pathways of differentiation. In some embodiments, the mesenchymal stem cells express CD105, CD73, and CD90, and do not express CD45, CD34, CD14, CD11b, CD79a, CD19, or HLA-DR. See Dominici et al., *Cytotherapy,* 2006, 8:315-317, incorporated by reference in its entirety.

In some embodiments, the mesenchymal stem cells do not express CD31 or CD133. See Lodie et al., *Tissue Engineering,* 2002, 8:739-751. In some embodiments, expression of CD44 depends on the serum concentration. See id.

In some embodiments, the mesenchymal stem cells express SH2, SH3, CD29, CD44, CD71, CD90, CD106, CD120a, CD124, and are negative for markers of the hematopoietic lineage, such as CD14, CD34, and CD45. See Pittenger et al., *Science,* 1999, 284:143-147.

In some embodiments, the mesenchymal stem cells are capable of differentiating into osteoblasts, adipocytes, and chondrocytes when exposed to the appropriate medium.

In some embodiments, the mesenchymal stem cells are derived from adipose, bone marrow, dental pulp, colon, heart, liver, lung, tonsil, umbilical cord, amnion, or fetal liver. Markers for the identification of these cell types are known in the art and provided, for example, in Table I of Signore et al., *J. Cell. Physiol.,* 2011, 227:3291-3300, incorporated by reference in its entirety.

In some embodiments, the mesenchymal stem cells support hematopoietic activity and have immunomodulatory activity. See Signore et al., *J. Cell. Physiol.,* 2011, 227:3291-3300, incorporated by reference in its entirety.

In some embodiments, the mesenchymal stem cells are lung mesenchymal stem cells as described, for example, in Ingenito et al., *Cell Transplantation,* 2012, 21:175-189, incorporated by reference in its entirety.

10. EXAMPLES

Example 1: Treatment of Horse with Granuloma Fluid

The present example provides methods and results for treating a horse suffering from exercise-induced pulmonary hemorrhage with a composition of provided herein.

HORSE #1, a four-year old thoroughbred, was evaluated prior to treatment following an easy gallop. Evaluation was by endoscopic examination of the trachea according to Hinchcliff, et al., 2005, J. Am. Vet Med. Assoc. 227:768-74.

Grade 0: No blood detected in the pharynx, larynx, trachea, or mainstem bronchi.

Grade 1: Presence of one or more flecks of blood or two or fewer short (less than one-quarter the length of the trachea) and narrow (less than 10% of the tracheal surface area) streams of blood in the trachea or mainstem bronchi (the two airways the trachea splits into; these carry air to and from the right and left lungs) visible from the tracheal bifurcation.

Grade 2: One long stream of blood (more than one-half the length of the trachea) or more than two short streams of blood occupying less than one-third of the tracheal circumference.

Grade 3: Multiple, distinct streams of blood, covering more than one-third of the tracheal circumference, with no blood pooling at the thoracic inlet.

Grade 4: Multiple, coalescing streams of blood covering more than 90% of the tracheal surface with blood pooling at the thoracic inlet.

Prior to treatment, HORSE #1 showed a bleeding score of 3 out of 4 after an easy gallop. The score was assigned by a practitioner using the scale above.

HORSE #1 received a first treatment including a full dose (10 cc) of granuloma powder (VivaStem-Equine Injection Kit; VivaStem Laboratories LLC) dissolved in saline solution and administered by nebulizer (Flexineb, Nortev) to the lungs. Following treatment at 24 hours, HORSE #1 jogged for one mile. At 48 hours, HORSE #1 galloped for 1.5 miles.

At 72 hours, HORSE #1 galloped for 1.5 miles. No bleeding was observed 24, 48, and 72 hours following treatment. A grade of 0/4 was assigned.

Eight days later, HORSE #1 received a second treatment of 10 cc dissolved granuloma powder, as described above. Following treatment at 24 hours, HORSE #1 had a mild jog. At 48 hours, HORSE #1 galloped for 1.5 miles. At 72 hours, HORSE #1 galloped for 1.5 miles. On endoscopic evaluation following treatment, no bleeding was observed 24, 48, and 72 hours following treatment. A grade of 0/4 was assigned.

Two weeks later, HORSE #1 was evaluated a third time, following a two minute effort at an average of about 15 seconds per ⅛ mile. On endoscopic evaluation, no bleeding was observed, and an endoscopic score of 0 was assigned.

After another week, HORSE #1 was evaluated a fourth time, following a two minute effort at an average of about 15 seconds per ⅛ mile. On endoscopic evaluation, no bleeding was observed, and an endoscopic score of 0 was assigned.

This example demonstrates that one and two administrations of a composition provided herein reduced bleeding in an exercise-induced pulmonary hemorrhage subject when evaluated by pulmonary endoscopy. The endoscopic score was reduced from ¾ on an initial evaluation to 0/4 on the standard scale used in the field.

11. EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

What is claimed is:

1. A method of treating exercise-induced pulmonary hemorrhage in a horse in need thereof, comprising:

(i) administering a first amount of a pharmaceutical composition comprising granuloma fluid, or a composition derived therefrom, to the horse, prior to exercise;

(ii) administering a second amount of the pharmaceutical composition comprising granuloma fluid, or a composition derived therefrom, to the horse after exercise, wherein the granuloma fluid or composition derived therefrom comprises stem cells in an amount of about $5\times10^4$ to about $5\times10^{11}$ cells.

2. The method of claim 1, wherein the pharmaceutical composition is administered systemically or locally.

3. The method of claim 1, wherein the pharmaceutical composition is administered by a route of administration selected from the nasal, pulmonary, inhalation, intraarterial, intradermal, intramuscular, intraperitoneal, intravenous, parenteral, and subcutaneous routes.

4. The method of claim 1, wherein the pharmaceutical composition is administered by a route of administration selected from the nasal and pulmonary routes.

5. The method of claim 1, wherein the subject is selected for treatment based on epistaxis, endoscopy, bronchoalveolar lavage, biopsy, radiograph, pulmonary scintigraphy, a history of exercise-induced pulmonary hemorrhage, or an elevated pulmonary blood pressure.

6. The method of claim 1, wherein the granuloma fluid, or composition derived therefrom, is administered to the subject at a dose that is equivalent to about 1 mg to about 20 g of granuloma powder.

7. The method of claim 1, wherein the granuloma fluid, or composition derived therefrom, is administered to the subject at a dose that is equivalent to about 200 mg to about 5 g of granuloma powder.

8. The method of claim 1, wherein pharmaceutical composition is administered with a further therapeutic agent.

9. The method of claim 8, wherein the further therapeutic agent is administered within 7 days of the pharmaceutical composition.

10. The method of claim 8, wherein the pharmaceutical composition comprises the further therapeutic agent.

11. The method of claim 8, wherein the further therapeutic agent is selected from furosemide, aclidinium, albuterol, arformoterol, beclomethasone, budesonide, ciclesonide, clenbuterol, corticosteroids, dexamethasone, fluticasone, formoterol, indacaterol, ipratropium bromide, levalbuterol, L-arginine, metaproterenol, mometasone, pirbuterol, salmeterol, sildenafil, tiotropium, and vilanterol, a cell, platelet-rich plasma, conditioned medium, and nasal strips.

12. The method of claim 1, wherein the composition derived from granuloma fluid is selected from a granuloma powder, a concentrated granuloma fluid, and a diluted granuloma fluid.

13. The method of claim 1, wherein the pharmaceutical composition is administered by a device selected from a nebulizer, a nasal sprayer, a metered dose inhaler, a dry powder inhaler, a cannula, a tracheal tube, an endotracheal tube, a tracheostomy tube, an intranasal tube, an endoscope, a transcutaneous transthoracic injection deice, a needle, or a single-pass low aerosolization method.

14. The method of claim 1, wherein the granuloma fluid, or composition derived therefrom, is from a horse.

15. The method of claim 1, wherein the granuloma fluid, or composition derived therefrom, is from a mammal that is of the same species as the subject.

16. The method of claim 1, wherein the granuloma fluid, or composition derived therefrom, is from a mammal that is of a different species from the subject.

* * * * *